United States Patent
Glynn

(10) Patent No.: US 7,654,671 B2
(45) Date of Patent: Feb. 2, 2010

(54) DEVICE FOR MONITORING BODY FUNCTIONS

(75) Inventor: Christopher Glynn, Gaunt Mill, Rack End, Standlake, Oxon OX8 7QA (GB)

(73) Assignee: Christopher Glynn, Oxford (GB)

( * ) Notice: Subject to any disclaimer, the term of this patent is extended or adjusted under 35 U.S.C. 154(b) by 0 days.

(21) Appl. No.: 11/814,933

(22) PCT Filed: Jan. 27, 2006

(86) PCT No.: PCT/GB2006/000280

§ 371 (c)(1),
(2), (4) Date: Jul. 9, 2008

(87) PCT Pub. No.: WO2006/079824

PCT Pub. Date: Aug. 3, 2006

(65) Prior Publication Data

US 2008/0278688 A1  Nov. 13, 2008

(30) Foreign Application Priority Data

Jan. 27, 2005  (GB) ................... 0501703.3

(51) Int. Cl.
*A61B 3/10* (2006.01)
(52) U.S. Cl. ...................... 351/221; 351/205
(58) Field of Classification Search ......... 351/200–246; 600/310–322
See application file for complete search history.

(56) References Cited

U.S. PATENT DOCUMENTS

| 4,848,340 | A | * | 7/1989 | Bille et al. ............... 606/4 |
| 5,325,133 | A | * | 6/1994 | Adachi ................. 351/209 |
| 6,045,226 | A |   | 4/2000 | Claessens ............. 351/205 |
| 2004/0233061 | A1 |   | 11/2004 | Johns ................. 340/575 |

FOREIGN PATENT DOCUMENTS

| WO | WO 90/12534 | 11/1999 |
| WO | WO 02/071932 A1 | 9/2002 |
| WO | WO 2004/034895 A1 | 4/2004 |
| WO | WO 2005/120878 A1 | 12/2005 |

OTHER PUBLICATIONS

International Search Report dated Mar. 22, 2006.

* cited by examiner

*Primary Examiner*—Mohammed Hasan
(74) *Attorney, Agent, or Firm*—KED & Associates LLP

(57) ABSTRACT

An optical system for non-invasive monitoring includes a light source to direct one or more pulses of light into an eye, a subject and a light receiver to receive light returning from the eye. The light receiver, or a processor coupled to the light receiver, records a frequency or intensity of the returning light at a selected timing relative to the one or more pulses of light from the light source. This timing may be selected to reduce a proportion of light reflected from a cornea, iris, or lens of the eye.

15 Claims, 5 Drawing Sheets

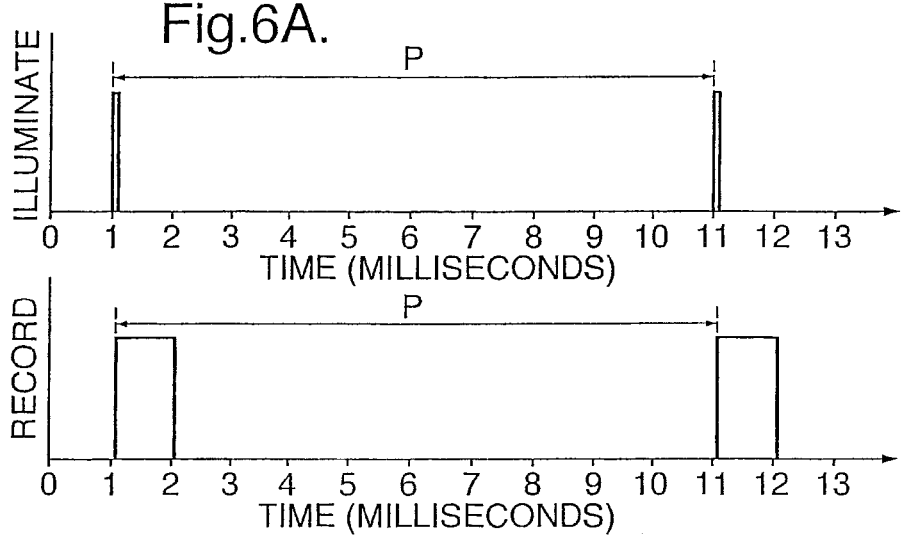
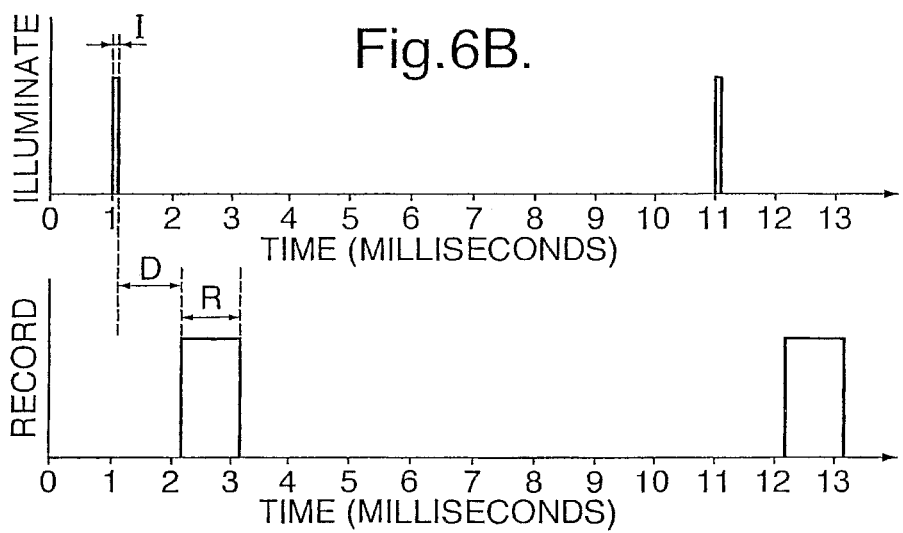
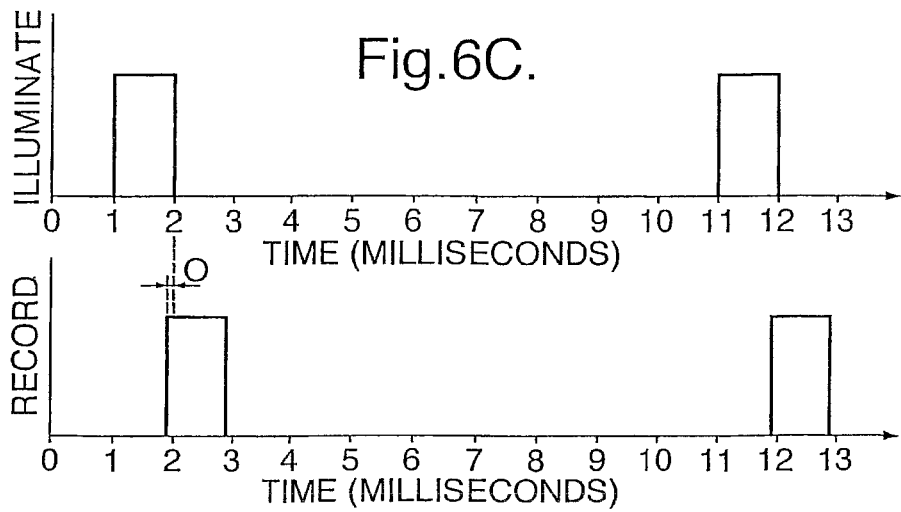

DEVICE FOR MONITORING BODY FUNCTIONS

TECHNICAL FIELD

The present invention relates to a device for use in non-invasive monitoring of a human or animal subject's bodily functions in vivo. The device relates, more particularly, to such monitoring that uses one or more light beams directed at, and returning from, various parts of the subject's eye(s) to provide analysable data.

BACKGROUND ART

Monitoring the functions of a human or animal body is necessary in many different situations. In the past, blood samples have been taken from the patient or animal and constituents have been measured by spectrophotometry. It is also known to measure the constituents in the blood of the patient or of the animal by bringing a spectrophotometer into contact with the patient or the animal, for example by using modified contact lens systems. The eye, which is the only part of the body that is designed to transmit light, thus acts as the curvette for the spectrophotometer.

WO90/12534 describes apparatus for monitoring body functions by directing light into the eye and analysing the light returning therefrom. It also describes a pupillometer for measuring the size of the pupil. WO02/071932 describes an improvement of this apparatus in which an alignment means determines the position of the centre of the pupil using a pupillometer to assist in aligning the optical system directing light into the eye. This disclosure of both these specifications is hereby incorporated in the current specification.

The present invention aims to provide a further improvement of the apparatus described in WO90/12534 and WO02/071932.

SUMMARY OF INVENTION

Thus, according to a first aspect of the invention, there is provided a device for use in non-invasive monitoring of a human or animal subject's bodily functions in vivo, having a first optical system which comprises:

a) illumination means for directing illumination light into the eye and for providing the illumination light in one or more pulses; and b) receiving means for receiving light returning from the eye as a result of illumination by the illumination light and arranged to record the frequency and/or intensity of such returning light intermittently at a selected timing relative to the pulse(s) of illumination light so as to reduce the proportion of light reflected from the cornea and/or iris and/or lens of the eye that is recorded.

The device is thus arranged to provide one or more pulses of illumination light to illuminate the interior of the eye and to record the returning light after each pulse of illumination, such that direct reflections from parts of the eye other than the retina are reduced or eliminated. The recording period may commence immediately at the end of the illumination pulse, or a predetermined time period thereafter or may overlap with the end of the illumination pulse. This significantly increases the signal:noise ratio for the recorded light. The majority of the returning light which is measured is thus light returning from the retina. Preferably, this is diffuse light which has undergone multiple reflections within the eye before exiting through the pupil. The arrangement is preferably such that the majority of illumination light reflected directly by other parts of the eye is not recorded. The eye is preferably used as an integrating sphere to ensure that illumination of the interior of the eye is not affected by spatial, angular or polarisation changes in the illumination light. As will be described further below, this provides further significant advantages over known devices (in which illumination and recording is carried out simultaneously).

The first optical system may be provided by modifying a standard spectrophotometer to record pulsed or intermittent light signals. The general principles of using such spectrophotometric techniques are described in WO90/12534 referred to above.

In the spectroscopy field, the eye is in effect the curvette of the body, since it is the only part of the body that is designed to transmit light. Thus, measurement of the characteristics of light reflected from the eye can give an indication of characteristics of bodily functions in general. In addition, the present invention enables the ability of the eye to act as an integrating sphere to be utilised.

In a preferred arrangement, the device comprises a second optical system for measuring the pupil size, e.g. by modifying a standard pupillometer, such as that described in U.S. Pat. No. 5,784,145. Further, the general principles of using pupillometry in this context are described in the applicant's previous International Patent Applications Nos. WO90/12534 and WO02/071932.

Preferably, the device is also provided with alignment means, such as that described in WO02/071932, controllable either directly by, or independently of, the subject, for example by use of manually operated lever(s), button(s), joystick(s) and/or one or more computer mice. The alignment means provides a variable focus capability to the system and may optionally operate in an automatic way without personal intervention from either the subject or the clinician. Indeed, activation of such alignment may also be automatically initiated by the first optical system, once the location of the pupil has been determined.

In one embodiment, the second optical system is adapted to determine the location of the edge(s) of the pupil(s), so as to allow calculation of the centre of the pupil(s). The second optical system may also be used to provide iris recognition to determine and record the identity of the subject.

Although it is preferred that the illumination light be focussed in the plane of the pupil, in some embodiments, this need not be done and the light simply directed towards the eye so as to enter through the pupil and illuminate the retina.

In one arrangement, the first and second light systems comprise one or more optical fibre(s) for transmitting light towards the eye(s). In a particularly preferred arrangement, the optical fibre(s) are arranged to function as both the light input means and the light receiving means.

The first light system may be arranged to monitor the intensity of light of a selected wavelength returning from the retina of the eye.

Alternatively, the first light system may be arranged to monitor the intensity of light of different wavelengths returning from the retina of the eye, thereby enabling an absorbance/reflectance characteristic of the retina to be determined.

The first and second optical systems may have parts in common. Thus, for example, the first and second receiving means may be provided by the same unit. Likewise, if desired, the first and second light systems may use the same processing means.

According to another aspect of the invention there is provided a method of non-invasive monitoring of a human or animal subject's bodily functions in vivo in which one or more pulses of illumination light are directed into the eye and the frequency and/or intensity of light returning from the eye as a result of such illumination is recorded intermittently at a timing relative to said one or more pulses selected so as to reduce the proportion of light reflected from the cornea and/or iris and/or lens of the eye that is recorded.

According to a further aspect of the invention, there is provided the use of a subject's eye as an integrating sphere in the optical monitoring of the retina of the eye for non-invasive monitoring of bodily functions in vivo.

Other preferred or optional features of the invention will be apparent from the following description and from the subsidiary claims of the specification.

The expression "human or animal subject's bodily functions" used herein is intended to include the wide variety of different functions that a medical or veterinary practitioner may wish to non-invasively monitor or measure. In particular, it is intended to include the monitoring of any substances and changes in the blood of the retina and any biochemical (organic or inorganic) changes in the cells of the retina of the subject. In addition, any or all of these changes can be monitored in conjunction with changes in the electrical, biochemical or pathological activity of the retina or of the brain.

The term "light" used herein is, unless otherwise specified, intended to include visible wavelengths and non-visible wavelengths such as infra-red, near infra-red and ultra-violet light, that are non-injurious to the eye and the structures contained within the eye. An advantage of using non-visible wavelengths is that the pupil size does not change when the eye receives such wavelengths. However, it can also be advantageous to use visible wavelengths as these may cause the pupil to constrict in size and, as discussed further below, the smaller the pupil size the more diffuse the light exiting through the pupil will be.

BRIEF DESCRIPTION OF DRAWINGS

The present invention will now be described in further detail by way of the following non-limiting examples with reference to the drawings, in which:

FIGS. 6A, 6B and 6C illustrate the relative timing of the illumination pulses and recording periods in three different regimes.

DESCRIPTION OF PREFERRED
EMBODIMENTS

Figure 1:
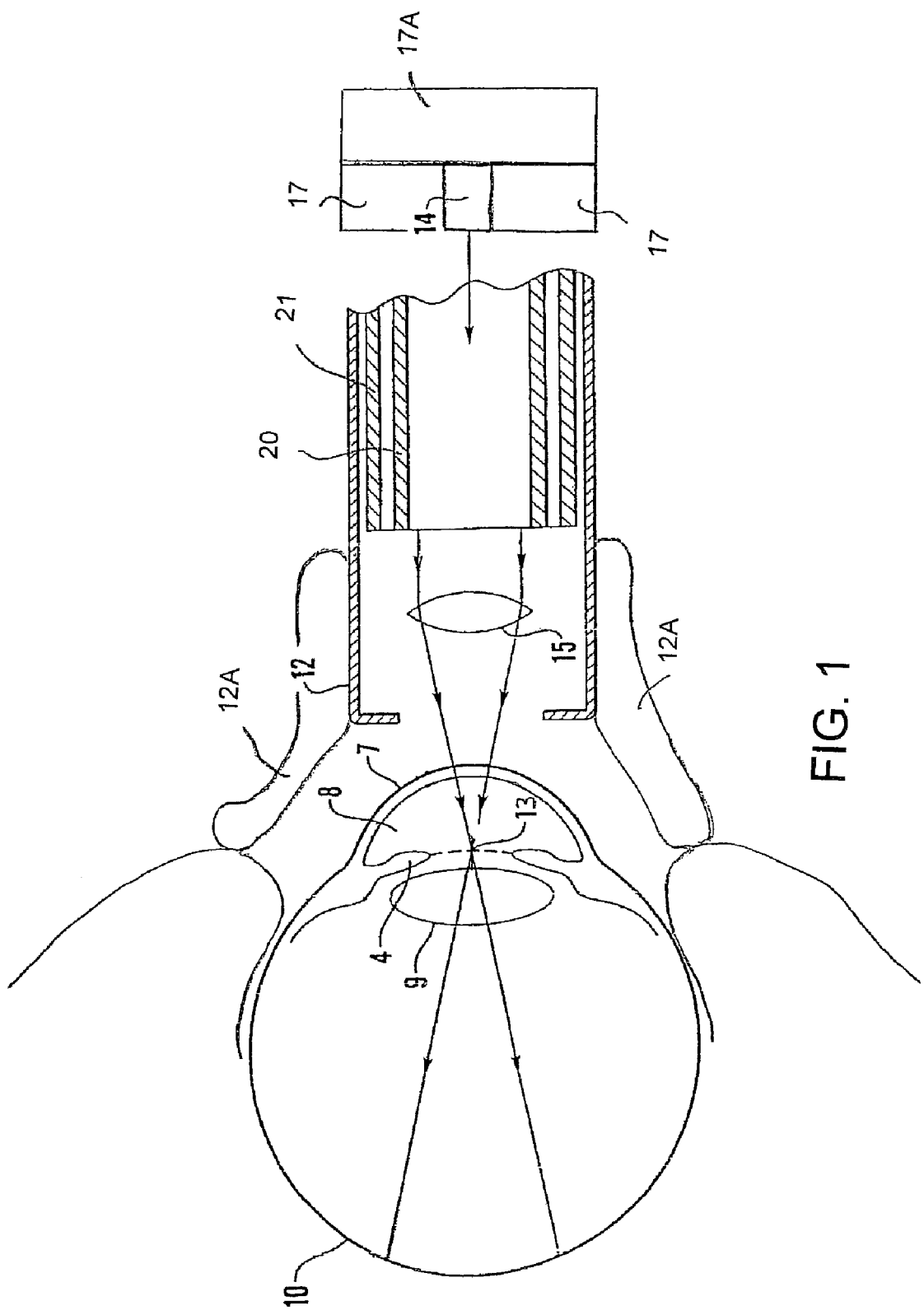
FIG. 1 shows a schematic representation of the first optical system of a first embodiment of the present invention during illumination of the interior of an eye.
Figure 2:
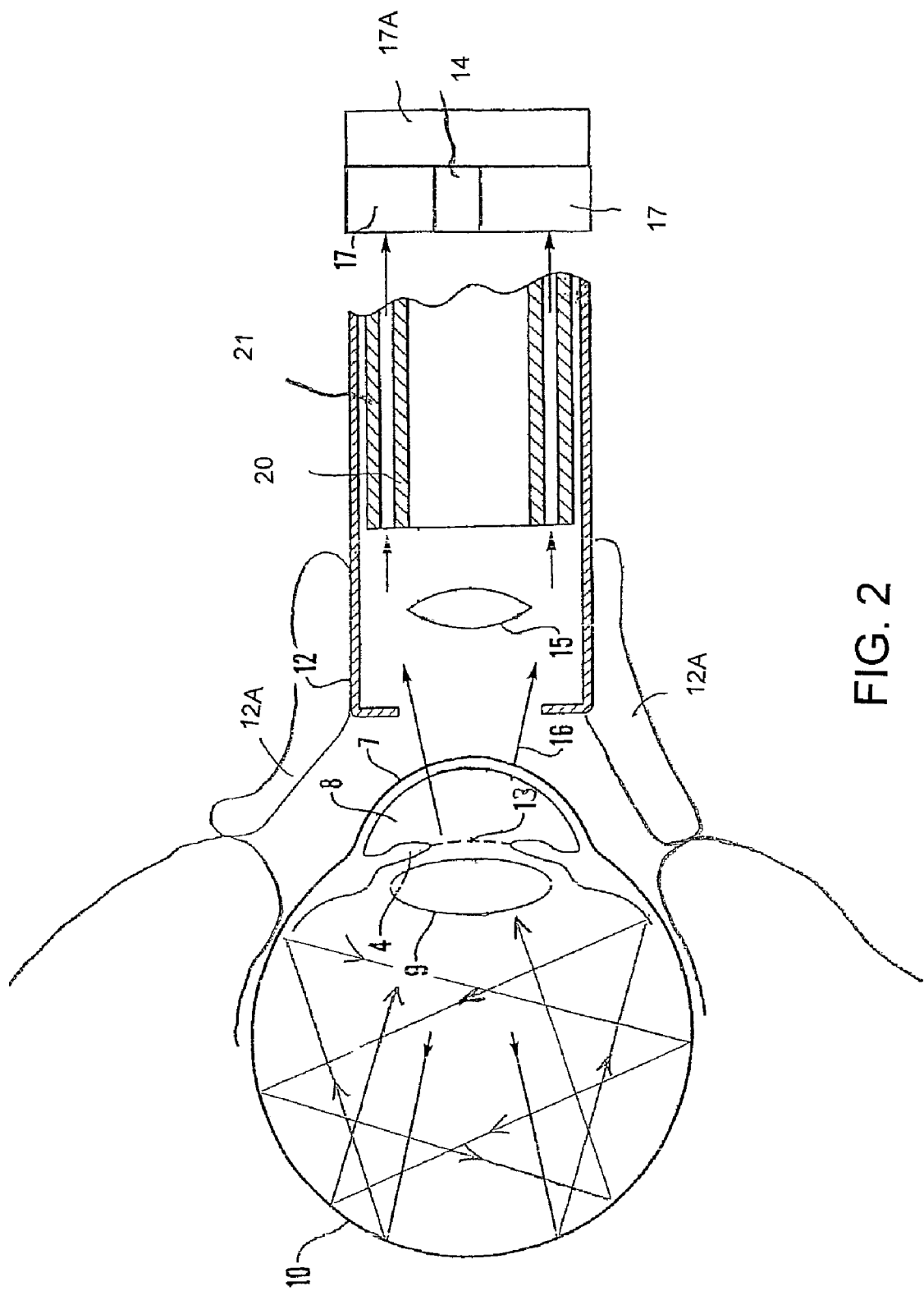
FIG. 2 shows a schematic representation of the first optical system of FIG. 1 during receipt of light returning from the eye.

In FIG. 1, a first optical system is shown that comprises a first light source 14 directing light to focussing means 15 mounted in a housing 12 for focussing light in the plane of the pupil 13 (so illumination is independent of pupil size) and directing the light onto the retina 10 of the eye. In FIG. 2, first receiving means 17 receives light returning from the eye through the pupil 13. FIG. 2 illustrates multiple reflection and scattering of the illumination light within the eye prior to the light emerging out of the pupil 13. Processing means 17A are provided for analysing the light that returns from the eye.

The first light source 14 is arranged to provide one or more pulses of illumination light, preferably a stream of pulses, and the receiving/processing means 17 is arranged to record the frequency and/or intensity of light returning from the eye intermittently at a selected timing relative to said pulses to reduce the proportion of light reflected from one or more of the cornea 7, iris 4 and lens 9 of the eye that is recorded, thereby improving the signal:noise ratio of the signal recorded. In a preferred arrangement, the light recorded is primarily recorded at a time or times when the light source 14 is not emitting light or is switched off. This may be achieved by intermittent actuation of the receiving means or appropriate sampling of the data received, e.g. by means of software. This means that the majority of the light recorded is light that is returning from the retina 10 that has undergone multiple reflections within the eye and is thus diffuse light. By this means, the eye is, in effect, being used as an integrating sphere.

It should also be noted that the smaller the pupil size, and hence the smaller the exit aperture for the light, the more diffuse the output light will be as more of the light will undergo multiple reflections before exiting through the pupil. The use of focussing means to focus light in the plane of the pupil so the eye can be illuminated through a small pupil (rather than dilating the pupil) is thus preferred.

An integrating sphere is an ideal optical diffuser and is used, for example, in radiometric measurements, where uniform illumination is essential. Light input into an integrating sphere is uniformly reflected and scattered around the sphere's interior so the output is a uniform, spatially integrated beam which is insensitive to spatial, angular or polarisation changes in the input light. Such variations lead to errors in measurements and can arise due to non-uniformity in the light source and/or in the optical path. Beam movements can arise due to movement of components or refractive index variation in the air path. Fibre optics can also be influenced by launch or fibre output pattern changes. Optical disk diffusers can be used to significantly reduce sensitivity to these effects but for critical measurements they are not sufficient. Use of an integrating sphere helps overcome such problems.

Integrating spheres are usually designed so there is not a direct path from the input to the output thereof. The input and output are thus usually located at different positions and baffles provided to block direct paths therebetween.

The present invention benefits from the realisation that the eye itself can be used as an integrating sphere so that measurements taken by the device are not subject to variations in the light source. However, as the eye only has a single input/output port, i.e. the pupil, and as light has to pass through reflective interfaces to enter the eye through the pupil, means have to be found to prevent input light which is reflected directly back by these interfaces from swamping the diffuse light which has undergone reflection within the eye. The present invention achieves this by the use of pulsed illumination and the selected timing of intermittent recording of light returning from the eye relative to the illumination pulses.

The present invention thus help avoid problems with direct reflections which arise in known devices and thus considerably increases the signal to noise ratio of the recoded signal. A further significant advantage of using pulsed illumination light is that this helps reduce problems, e.g. due to heating, which can arise if the retina receives too much illumination from the light source 14. Heating can alter the properties of the blood as well as cellular and metabolic activity and may cause damage to the eye. The use of steady, continuous illumination, whilst enabling measurements to be made in carefully controlled conditions, e.g. in a laboratory, may preclude use in a practical device, particularly if measurements need to be taken frequently, e.g. every day.

In addition, by providing illumination pulses over a relatively short period, e.g. for a few milliseconds, and recording light received during this period, the pulsatable component, i.e. variation in the quantity being sensed due to the pulsing blood flow in the blood vessels of the retina, can be reduced or eliminated. In contrast, the prior art which illuminates the retina continuously has to provide complex systems for recording measurements in time with the pulses in the blood flow to eliminate the pulsatable component.

The length of each pulse of illumination and the wavelength used will differ in dependence upon the substance or reaction to be measured. Typically, each illumination pulse may last between 0.1 milliseconds and a few seconds. The interval between illumination pulses will also depend on the substance or reaction being measured but, typically, would also be in the range 0.1 milliseconds to several seconds.

Although a single pulse could be used, the eye is preferably illuminated by a train of at least six pulses, and preferably more, with a measurement being recorded after each pulse and a mean and standard deviation calculated.

FIGS. 6A, 6B and 6C illustrate the timing of the illumination pulses and the recording periods in three different regimes:
1. Illumination period of 0.1 milliseconds and recording immediately after the pulse then repeat six times at intervals of 10 milliseconds (FIG. 6A).
2. Illumination period of 0.1 milliseconds, record after illumination has been off for 1 millisecond and then repeat this cycle six times with a 10 millisecond gap between each cycle (FIG. 6B).
3. Illuminate for 1 millisecond, start recording 0.1 milliseconds before the end of the illumination period for 1 millisecond and repeat for six cycles with a 10 millisecond gap between each cycle (FIG. 6C).

The following time intervals are shown in FIGS. 6A, 6B and 6C:
P: period between each illumination pulse and each recording interval, e.g. 10 milliseconds.
I: duration of an illumination pulse, e.g. 0.1 or 1.0 milliseconds.
R: duration of a recording period, e.g. 1.0 milliseconds.
D: delay between end of illumination pulse and commencement of recording period, e.g. 1.0 milliseconds.
O: overlap between illumination pulse and recording period, i.e. time interval between commencement of recording period and end of illumination pulse, e.g. 0.1 milliseconds.

As indicated above, the various time periods and intervals (P, I, R, D, O) will vary depending upon the specific application.

The first optical system may be self-supporting, e.g. be part of apparatus in front of which the subject is located. The subject positions his eye so as to receive the illumination light. Preferably, a flexible cowl 12A is provided around the housing 12 against which the subject can rest his eye. The cowl 12A may also serve to exclude extraneous light from the eye where the ambient light includes frequencies that are being monitored. Such cowls are well-known on other optical instruments e.g. around the lens of a telescope or pair of binoculars. The cowling also helps locate the subject's eye relative to the device.

As described in WO02/071932, a second optical system (not shown) may be used to locate the centre of the pupil 13, and alignment means (not shown) used to align the illumination light from the first optical system so that light is shone through the centre of the pupil 13 in the plane of the pupil 13, that is in a Maxwellian view. The alignment process can be effected, for example, by means of a joystick (not shown), which can be operated by the physician, or the subject themselves. In this way, the operator can view an image of the eye being investigated on a screen (not shown) and use the joystick to align the first optical system with the centre of the pupil 13. Further details of this alignment process are known from WO90/12534 so will not be described further.

However, the device may also be arranged such that the second optical system operates automatically (i.e. without manual operation). Thus, the second optical system may directly activate the alignment means to position the first optical system into the required alignment with the pupil.

Further, instead of the operator viewing the image of the eye on a screen, the image may be transferred directly onto the retina of the operator, for example by way of the first optical system itself.

As shown in FIG. 1, input light 14 is directed via an optical fibre 20 from which it is emitted so as to pass through focussing means 15 towards the centre of the pupil 13. As shown in FIG. 2, light 16, which returns from the eye back through the pupil 13, subsequently passes back into the device and travels as a beam along one or more optical fibres 21 to the receiving means 17.

The processing means 17A analyses the beam, e.g. to determine the absorbance/reflectance spectrum of the retina and/or the retinal blood vessels. Any combination of monochromatic lights or white light, as well as wavelengths in the infra-red, near infra-red or ultra-violet spectra can be used. Specific, selected wavelengths permit optimal discrimination of the various blood components, as well as optimal discrimination of the various retinal biochemical functions and components.

In this way, it is, for example, possible to provide an accurate measurement of the oxygen saturation of the retinal blood flow and, since this is more proximal to blood flow in the toe, finger or ear (as measured by well known prior techniques), it can provide the clinician with a more accurate assessment of the oxygen content of blood delivered to the brain.

Figure 3:
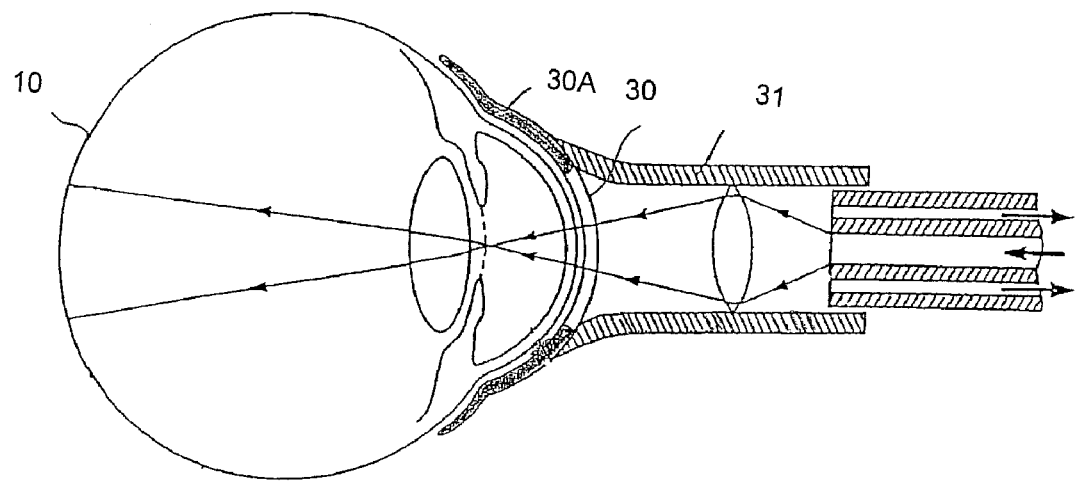
FIGS. 3 and 4 are schematic representations of the first optical system of a second embodiment of the eye during illumination of the eye and receipt of light returning therefrom, respectively.
Figure 4:
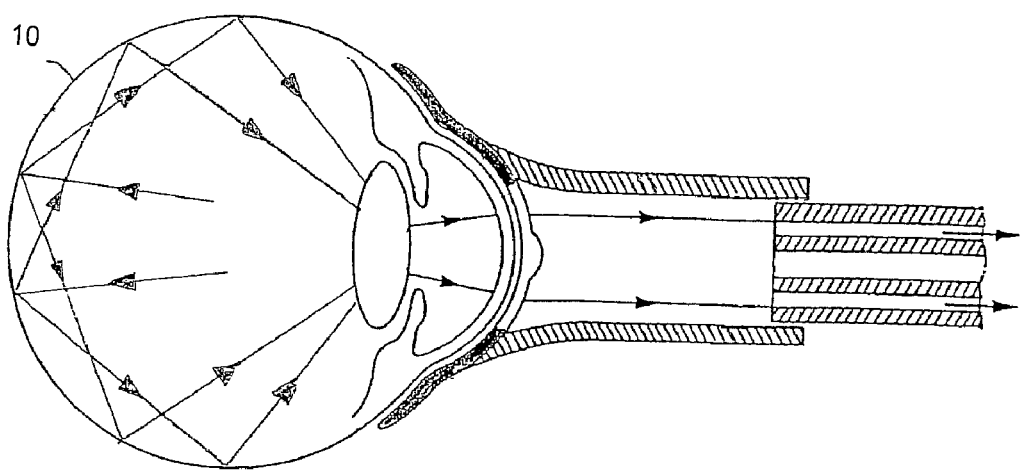

FIGS. 3 and 4 correspond to FIGS. 1 and 2 but show a device in which part of the optical system is mounted on a scleral contact lens 30. The use of such a lens 30 to support the device is described further in WO90/12534. Portions 30A of the contact lens extending beyond housing 31 may be coloured black if it is desirable to exclude extraneous light from entering the device. The operation of the device shown in FIGS. 3 and 4 is otherwise similar to that shown in FIGS. 1 and 2.

Figure 5:
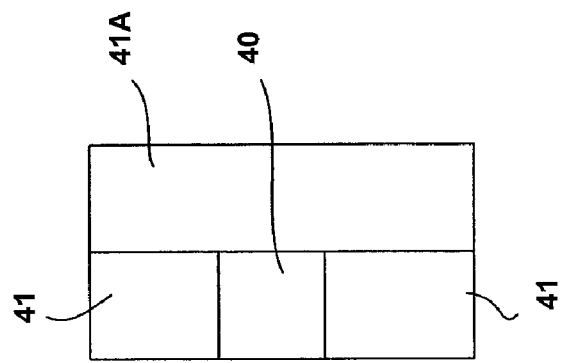
FIG. 5 is a schematic representation of a third embodiment of the invention.
Figure 5:
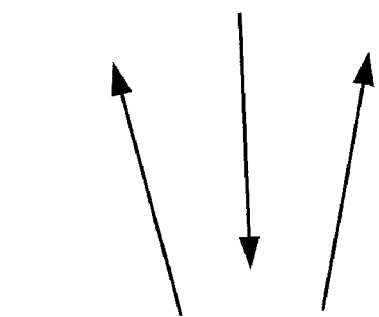
Figure 5:
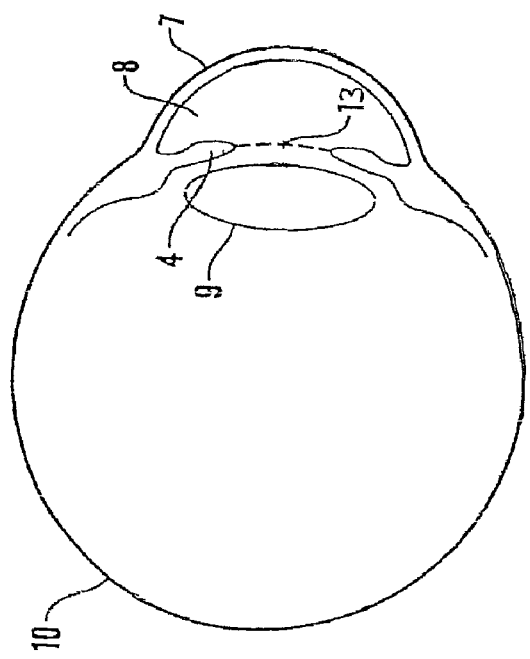

In a further arrangement, shown schematically in FIG. 5, the illumination means 40 and receiving means 41 may be located remotely from the eye but positioned to direct illumination into the eye and receiving light returning therefrom. Processing means 41A is also shown. In this embodiment, the illumination light need not be focussed in the plane of the pupil but simply directed into the eye.

The system described above can be used for a wide range of applications. For example, it is possible to measure any, or all, of the constituents of the blood of a subject, in vivo. Additionally, when appropriate wavelengths are used, it is also possible to measure the constituents of the cells of the retina or to measure physiological and or pathological changes in the cells of the retina. It is possible to measure the biochemical activity of these cells, in real time.

The illumination and recording of light may be used in a variety of analysis methods, e.g. to monitor the absorbance of specific wavelengths, to carry out diffuse reflectance spectroscopy, to carry out Raman spectroscopy (in which the illuminating light stimulates light emission from the eye which is then detected) or fluoroscopy.

Further, it is possible also to use the system to measure the unique DNA profile of any individual and thus provide security checks. For example, a monocular system can be used as part of a cash-dispensing machine, in which the identity of the person wishing to withdraw cash is checked via non-invasive DNA analysis of the retinal cells. Alternatively, or additionally, the second optical system may be used to identify the subject by iris identification.

Identification of the subject in this may be used for security and/or legal reasons. It may also be used by the processing means 17A to associate the subjects identity with the measurements being taken for recording purposes.

Whereas police currently use breathylisers to check a driver's blood alcohol levels at the road side, using the present system would not only allow such analysis to be more accurately performed, but would also allow analysis of any number of other drugs that can be detrimental to driving, which may also be present in a driver's blood. This analysis can be linked with detection of the identity of the driver (as described above) to record who has been tested in this way and/or check whether that person is recorded as an authorised driver of the vehicle.

Similar tests may be used to monitor operators of other types of machinery.

The system is also more suitable for monitoring the blood glucose levels of diabetic patients than conventional needle-based methods, since it is non-invasive.

It is also possible to measure changes in the arteries and veins of the retina, which may be an indication of generalised arterial and venous disease. Thus, in diabetic patients, who typically can suffer from such generalised arterial disease, it would be possible to non-invasively chart the progression of the disease.

The system can measure visual evoked potentials more accurately than conventional means, because it is possible to give an accurate amount of light and so the amplitude of response can also be assessed. Conventionally, by contrast, only latency of response is measured. Thus, the present system allows for the assessment of any electrical activity of the retina, so that the activity of the visual areas of the brain can be assessed.

The measurements made possible with the present system can be of static samples or of continuous samples in real time.

Hence, in general, the system in effect provides the subject with the resources of a non-invasive, real time biochemical and haematological laboratory.

The invention claimed is:

1. A device for use in non-invasive monitoring of a human or animal subject's bodily functions in vivo, having a first optical system which comprises:
   a) a light source to direct light into an eye of the human or animal subject, the light source directing the light in one or more pulses; and
   b) a light receiver to receive light returning from the eye as a result of illumination by the light from the light source, the light receiver or a processor coupled to the light receiver arranged to record at least one of a frequency or intensity of the returning light at a selected timing relative to the one or more pulses of light from the light source, said timing selected so as to reduce a proportion of light reflected from at least one of a cornea or iris or lens of the eye, wherein a focal point of the one or more pulses of light from the light source lies in a plane that is at least substantially coincident with a plane of the pupil of the eye.

2. A device as claimed in claim 1, wherein the light receiver or processor is arranged to record at least one of the frequency or intensity of diffuse light received back from the eye.

3. A device as clamed in claim 2, wherein the light receiver or processor is arranged to record light that has undergone multiple reflections within the eye, and wherein the eye is used as an integrating sphere so that illumination of the interior of the eye is insensitive to variations in the light receiver.

4. A device as claimed in claim 1, wherein the light receiver or processor is arranged to monitor the intensity of light of a selected wavelength returning from the a retina of the eye.

5. A device as claimed in claim 1, wherein the light received by the receiver is processed in which the first optical system is arranged to determine a DNA profile to identify a subject of the eye.

6. A device as claimed in claim 1, wherein a second optical system arranged to determine a location of the pupil of the eye based on the light received by the light receiver of the first optical system.

7. A device as claimed in claim 6, wherein the second optical system is arranged to identify a subject by iris identification based on the light received by the light receiver of the first optical system.

8. The device as claimed in claim 1, wherein directing the one or more pulses of light in said plane allows light beams to be reflected within the eye based on a pattern which substantially conforms to an integrating sphere, the returned light received as a result of being reflected based on said pattern being independent from variations in the light source.

9. The device as claimed in claim 1, wherein directing the one or more pulses of light in said plane allows light beams to be reflected within the eye in a uniform pattern, so as to reduce the proportion of light directly reflected from the iris, cornea, or lens of the eye in the returned light received by the light receiver.

10. A device for use in non-invasive monitoring of a human or animal subject's bodily functions in vivo, having a first optical system which comprises:
    a) a light source to direct light into an eye of the human or animal, the light source directing the light in one or more pulses; and
    b) a light receiver to receive light returning from the eye as a result of illumination by the light from the light source, the light receiver or a processor coupled to the light receiver arranged to record at least one of a frequency or intensity of the returning light at a selected timing relative to the one or more pulses of light from the light source, so as to reduce a proportion of light reflected from at least one of a cornea or iris or lens of the eye,
    wherein the light receiver or the processor is arranged to record at least one of the frequency or the returning light during a recording period after each pulse of light, the recording period commencing at an end of said each pulse of light or at a predetermined time interval before or after the end of said each pulse of light.

11. A device for use in non-invasive monitoring of a human or animal subject's bodily functions in vivo, having a first optical system which comprises:
    a) a light source to direct light into an eye of the human or animal, the light source directing the light in one or more pulses; and
    b) a light receiver to receive light returning from the eye as a result of illumination by the light from the light source, the light receiver or a processor coupled to the light receiver arranged to record at least one of a frequency or intensity of the returning light at a selected timing relative to the one or more pulses of light from the light source, so as to reduce a proportion of light reflected from at least one of a cornea or iris or lens of the eye, wherein the light receiver or processor is arranged to monitor the intensity of light of different wavelengths returning from a retina of the eye, thereby allowing an absorbance or reflectance characteristic of the retina to be determined.

12. A method of non-invasive monitoring of a human or animal subject's bodily functions in vivo, said method comprising:

directing one or more pulses of light into an eye of the human or animal subject;

intermittently recording light returning from the eye at a timing relative to directing of said one or more pulses; and determining at least one of a frequency or intensity of light returned from the eye, wherein said timing is selected so as to reduce a proportion of light reflected from a cornea or an iris or a lens of the eye, wherein a focal point of the one or more pulses of light from the light source lies in a plane that is at least substantially coincident with a plane of the pupil of the eye.

13. The method as claimed in 12, wherein the eye is used as an integrating sphere in optical monitoring of a retina of the eye.

14. The method as claimed in claim 12, wherein directing the one or more pulses of light in said plane allows light beams to be reflected within the eye based on a pattern which substantially conforms to an integrating sphere, the returned light received as a result of being reflected based on said pattern being independent from variations in a light source.

15. The method as claimed in claim 12, wherein directing the one or more pulses of light in said plane allows light beams to be reflected within the eye in a uniform pattern, so as to reduce the proportion of light directly reflected from the iris, cornea, or lens of the eye in the returned light received by a light receiver.

* * * * *